(12) United States Patent
Jörimann et al.

(10) Patent No.: US 6,583,391 B2
(45) Date of Patent: Jun. 24, 2003

(54) MODULATION METHOD AND APPARATUS FOR THERMALLY ANALYZING A MATERIAL

(75) Inventors: Urs Jörimann, Bertschikon (CH); Thomas Hütter, Niederrohrdorf (CH)

(73) Assignee: Mettler-Toledo GmbH, Greifensee (CH)

(*) Notice: Subject to any disclaimer, the term of this patent is extended or adjusted under 35 U.S.C. 154(b) by 318 days.

(21) Appl. No.: 09/773,783

(22) Filed: Jan. 31, 2001

(65) Prior Publication Data

US 2001/0019049 A1 Sep. 6, 2001

(30) Foreign Application Priority Data

Feb. 3, 2000 (EP) .......................................... 00102396

(51) Int. Cl.$^7$ ................................................. H05B 1/02
(52) U.S. Cl. .................... 219/497; 219/494; 374/11; 374/135
(58) Field of Search .................... 219/497, 494, 219/506, 501, 502; 374/10, 11, 33, 135, 121

(56) References Cited

U.S. PATENT DOCUMENTS

| 5,288,147 A | 2/1994 | Schaefer et al. | |
|---|---|---|---|
| 5,346,306 A | * 9/1994 | Reading et al. | 374/10 |
| 5,624,187 A | * 4/1997 | Reading | 374/11 |
| 6,390,669 B1 | * 5/2002 | Nakamura et al. | 374/12 |

FOREIGN PATENT DOCUMENTS

| EP | 0559362 | 9/1993 |
|---|---|---|
| EP | 0645619 | 3/1995 |
| EP | 0701122 | 3/1996 |
| EP | 0747694 | 12/1996 |
| EP | 0785423 | 7/1997 |
| WO | 9533199 | 12/1995 |
| WO | 9533200 | 12/1995 |

OTHER PUBLICATIONS

E. Lebsanft: "A High-Sensitiveity Heat Flow Calorimeter For The Investigation of Metal-Hydrogen Reactions" Journal of Physics E. Scientific Instruments, Bristol, vol. 12, No. 8, Aug. 1, 1979, pp 699–705.

* cited by examiner

Primary Examiner—Mark Paschall
(74) Attorney, Agent, or Firm—Friedrich Kueffner

(57) ABSTRACT

A method and apparatus for thermally analyzing a sample of a material by detecting a heat flow between the sample (7) and a heat source (1) and evaluating a functional relation between the measured heat flow (HF) and an associated temperature is based on controlling the heating power of the heat source (1) so as to cause the heat source to follow a temperature program (17) as a function of time superposed with a modulation (23) of the heating power.

20 Claims, 4 Drawing Sheets

MODULATION METHOD AND APPARATUS FOR THERMALLY ANALYZING A MATERIAL

BACKGROUND OF INVENTION

The present invention relates to a method for thermally analyzing a material, comprising the steps of establishing a heat flow path between a sample of said material and a heat source to thereby cause a flow of heat between said sample and said heat source, controlling the heating power of said heat source as a function of time, measuring a signal representative of said heat flow between said sample and said heat source and a signal representative of a temperature associated with said heat flow, and evaluating a functional relation between said measured heat flow and temperature signals; and to an apparatus adapted for carrying out said method.

In the thermal analysis of materials, a sample of the material is heated by the heat source, and the flow of heat between the heat source and the sample is evaluated to thereby derive structural and compositional information about the material, in particular heat capacity, phase transitions, onset temperatures, etc. In particular, for the sake of accuracy and dynamic range, differential methods, e.g. differential scanning calorimetry (DSC), are being used. In these differential methods, a reference material is arranged in the heat flow symmetrically with respect to the sample to be analyzed, and the analysis is performed on the basis of the differential heat flow between the sample and reference materials.

EP 0 559 362 A1 discloses a differential method wherein the temperature of the heat source is controlled in accordance with a predetermined temperature program so as to cause said heat source temperature to vary in correspondence with a linear rise of temperature superposed by a periodic temperature modulation having a predetermined modulation amplitude and frequency. A deconvolution technique is used to derive from the differential heat flow signal two separate signal components caused by the linearly changing component and the modulation component of the heat source temperature, respectively.

WO95/33199 and WO95/33200 similarly disclose differential methods wherein a temperature of the heat source is driven through a predetermined temperature program, said temperature program comprising two linearly changing parts of the same time duration in the first case and a linearly changing part superposed with a periodically changing part having a predetermined amplitude and frequency in the second case. The differential heat flow signal and a phase difference between the differential heat flow signal and the programmed temperature of the heat source are evaluated to separately derive a real and an imaginary signal portion.

In these conventional methods, the thermal excitation of the sample is thus due to a linear rise in temperature combined with a temperature modulation of a selected amplitude and frequency. Since the resulting heat flow signal is dependent on the sample to be analyzed, and is therefore unknown, a problem arises how to select the temperature modulation. If the selected modulation amplitude is too small for the specific sample, the heat flow signal is too small, and the results are inaccurate. In contrast, if the selected temperature modulation amplitude is too big, the transfer of heat flow with the sample is too large thereby destroying the thermal event to be analyzed. This leads to time-consuming trial-and-error experiments until the appropriate temperature modulation amplitude is found.

SUMMARY OF INVENTION

It is an object of the present invention to provide for a method for thermally analyzing a material which is better adapted to heat flow requirements in each experiment and type of sample. It is a further object to provide for an apparatus which is capable of carrying out this method.

Having regard to the method, this object is attained in accordance with the invention in that said step of controlling said heating power is based on a first control input for causing said heat source to assume a predetermined temperature as a function of time and a second control input for modulating the heating power of said heat source caused by said first control input in accordance with a selected periodic power modulation.

According to the present invention, the user directly selects a modulation of the heating power of the heat source required for the experiment instead of selecting a temperature modulation for the heat source. This enables the user to directly determine the optimum heating power requirements for his individual experiment.

The terms "heating", "heat flow", "heat source" and related terms are to be understood in the context of the present specification to mean either heating or cooling. In the latter case, the "heat source" will e.g. be a source of cooling agent thermally coupled to the sample.

The first control input for causing the heat source to assume a predetermined temperature as a function of time generally includes any temperature-versus-time function which varies with time considerably slower than the periodic power modulation caused by the second control input does. A particularly interesting specific case includes to vary the temperature of the heat source by the first control input in accordance with a linear temperature program which means a selected constant heating rate. Selecting the heating rate to be zero also includes the isothermic case where the temperature of the heat source is controlled to be constant at a selected temperature value by the first control input.

In one embodiment of the invention, the second control input is to set a predetermined amplitude of said power modulation. In this case, while both of the amplitude and frequency of the power modulation are fixed, the resulting temperature modulation of the heat source does no longer have a constant amplitude.

In another embodiment, the second control input is to determine said power modulation so as to result in a predetermined amplitude of said measured heat flow. This selects a constant amplitude of the measured heat flow while again the measured temperature amplitude is generally not constant.

It is useful to embody the invention so as to further comprise the steps of measuring a temperature of said heat source, filtering said measured temperature to thereby derive an average temperature corresponding to the unmodulated heating power of said heat source, and using a signal representative of a difference between said average temperature and said first control input as a heating power control signal for said heat source. The result is a first control loop which causes the average temperature to follow the unmodulated temperature-versus-time function commanded by the first control input.

When it is desired to control the amplitude of the resulting measured heat flow, it is useful for the method to further comprise the steps of demodulating said measured heat flow signal to thereby derive an amplitude of said heat flow caused by said power modulation, and using a signal representative of a difference between said demodulated amplitude and said second control input as a heating power control signal for said heat source. This corresponds to a second control loop causing the amplitude of the measured heat flow to assume an amplitude value commanded by the second control input.

The method according to the invention may be embodied so as to further comprise the steps of providing a supplementary heat source in addition to said heat source, controlling said heat source in accordance with said first control input, and controlling said supplementary heat source in accordance with said second control input. In this case, the heat source provides for the predetermined temperature-versus-time function while the supplementary heat source provides for the selected power modulation.

Preferably, the signal representative of heat flow is a differential signal corresponding to a difference of heat flows between said sample and said heat source and a reference material and said heat source. This provides for high accuracy and wide dynamic range since only the difference in heat flowing into or out of said sample as compared to the heat flowing into or out of a known reference material is used for the purposes of analysis, and there is no need for an absolute measurement.

In the case of differential analysis, the supplementary heat source may be associated with said sample only. This means that only the sample is exposed to the effect of the power modulation while the reference material is only subject to the effect of the temperature-versus-time function commanded by the first control input.

According to another important aspect, the method according to the present invention comprises the steps of deriving an average component of at least one of said measured heat flow and a heating rate derived from said measured temperature associated with said heat flow over a selected interval of time, deriving a dynamical component of at least one of said heat flow and heating rate as a difference between said measured heat flow or derived heating rate, respectively, and said respective derived average component, deriving an average temperature of said measured temperature associated with said heat flow over said selected interval of time, and representing at least one of said dynamical components as a function of said derived average temperature.

The dynamical component obtained by this type of evaluation is related to the power modulation of the heat source commanded by the second control input while the average component is related to the temperature-versus-time function commanded by the first control input.

While each of the heat source temperature or reference temperature could be used as a temperature associated with the heat flow, it is preferred that a temperature of said sample material is measured and is used as said signal representative of a temperature associated with said heat flow in the step of evaluating a functional relation between said measured heat flow and temperature signals.

The step for measuring the signal representative of the heat flow between the sample and the heat source and/or the reference and the heat source may advantageously be performed by measuring a temperature difference between at least two locations spaced at a distance along the respective heat flow path.

In order to perform the method in accordance with the invention, an apparatus for thermally analyzing a material comprising a heat source, a sample holder having a sample position thermally coupled to said heat source to thereby establish a heat flow path for a flow of heat between said heat source and a sample in said sample position, a controller for controlling the heating power of said heat source as a function of time, means for measuring a signal representative of said heat flow between said sample in said sample position and said heat source, means for measuring a signal representative of a temperature associated with said heat flow, and means for evaluating a functional relation between said measured heat flow and temperature signals is in accordance with the invention characterized in that said controller comprises means for setting a first control signal representing a selected temperature program of said heat source as a function of time and means for setting a second control signal representing a periodic power modulation of said heating power caused by said first control signal.

In the apparatus in accordance with the invention, the means for setting the second control signal may operate in various ways for selecting the parameters of the power modulation. It may e.g. be adapted to set a selected amplitude and a selected modulation frequency for the power modulation caused by the controller. Alternatively, it may be adapted to set a desired amplitude of the measured heat flow, and the controller in response thereto causes the power modulation to be performed so as to result in the set heat flow amplitude.

Specific embodiments of the apparatus in accordance with the invention are set out in subclaims 11 to 20.

In the following description, the method for thermally analyzing a material in accordance with the invention is exemplarily explained in conjunction with an apparatus adapted for performing the method with reference to the accompanying drawings, in which:

DETAILED DESCRIPTION OF DRAWINGS

Figure 1:
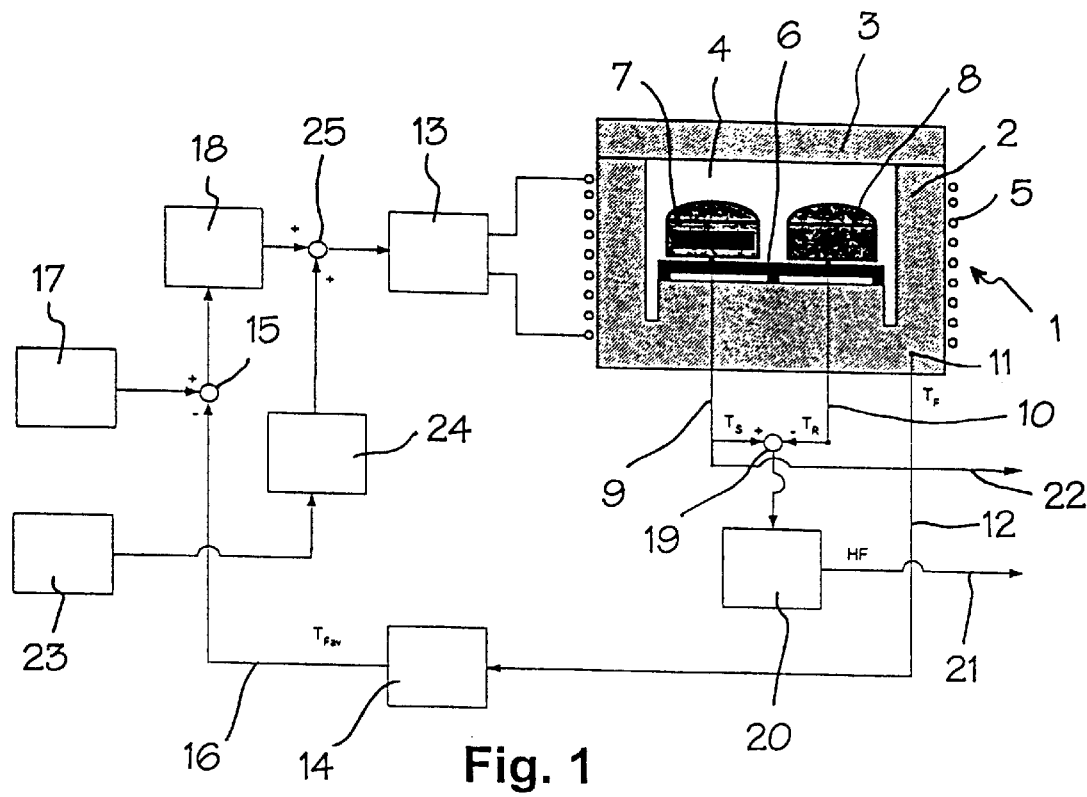
FIG. 1 is a schematic diagram of an embodiment of an apparatus for thermally analyzing a material.

FIG. 1 schematically illustrates a heat source 1 having an essentially hollow cylindrical oven block 2 made of silver. The upper face of oven block 2 is formed as a removable lid 3 for opening and closing block 2 to permit access to the interior 4 thereof. A winding of heating wire 5 is wound onto the exterior cylindrical surface of oven block 2 to provide for resistive heating. Alternatively, a flat resistive heater could be applied to the lower face of oven block 2 opposite to lid 3 or any other suitable portion of oven block 2.

A disc-shaped substrate 6 is arranged in the interior of oven block 2 in thermal contact therewith. Substrate 6 has two circular areas thereof formed as a sample holder and a reference holder, respectively, adapted to support a sample pan 7 and a reference pan 8, respectively. Each of the circular areas of the sample and reference holders are formed with a thermocouple arrangement for detecting the temperatures Ts and $T_R$ of the sample and reference pans 7, 8, respectively. The electrical signals representing the sample and reference temperatures $T_S$ and $T_R$, respectively, are fed to the outside of heat source 1 by means of signal lines 9 and 10, respectively. A platinum thermometer 11 arranged at the bottom portion of oven block 2 detects a temperature $T_F$ of oven block 2, and a corresponding electrical signal is fed to the outside by signal line 12. Electrical heating power is supplied to heater winding 5 of heat source 1 by a power amplifier 13.

The signal on signal line 12 representing the measured temperature $T_F$ of heat source 1 is applied to the input of a filter 14 which produces a signal representative of an average temperature $T_{Fav}$, at an output thereof. This average temperature signal is applied to one input of a subtractor 15 via signal line 16. The other input terminal of subtractor 15 is connected to the output of a temperature programmer 17. Temperature programmer 17 outputs a first control signal which represents a temperature-versus-time function for heat source 1. The output signal of subtractor 15 being representative of the difference between the first control signal from temperature programmer 17 and the average temperature signal $T_{Fav}$ on signal line 16 is applied to a control input of a temperature controller 18 which generates a corresponding control signal for power amplifier 13. As a result, the control loop formed by signal line 12, filter 14, signal line 16, temperature programmer 17, subtractor 15, temperature controller 18 and power amplifier 13 drives the heater winding 5 so that the average temperature $T_{Fav}$ of heat source 1 follows the temperature-versus-time function commanded by temperature programmer 17.

As it is well known in conventional calorimetry, the heat flow between a sample in sample pan 7 and the heat source 1 is proportional to a difference between the sample temperature $T_S$ and the heat source temperature $T_F$, while in the case of a differential method the differential heat flow HF is proportional to the difference between sample and reference temperatures $T_S$ and $T_R$, respectively. Based on this, signal lines 9 and 10 carrying the sample and reference temperature signals $T_S$ and $T_R$, respectively, are connected to the input side of a subtractor 19 which produces a corresponding difference signal on the output side thereof. This difference signal is applied to a heat flow calculation unit 20, and the calculated heat flow HF and the measured sample temperature $T_S$ are fed to an evaluation unit (not shown) on signal lines 21 and 22, respectively, for further processing which includes the evaluation of a functional relation between heat flow HF and temperature $T_S$. An alternative exemplary way of obtaining the heat flow HF is described herein below with reference to FIG. 7.

A power modulation programmer 23 outputs a second control signal representing a periodic power modulation, e.g. in terms of a modulation amplitude and frequency of heating power applied to heat source 1. This second control signal is applied to a control input of a power modulation generator 24 to thereby command power modulation generator 24 to produce an output signal for controlling power amplifier 13 in accordance with the selected modulation. The modulation control signal from power modulation generator 24 is superposed on the temperature control signal from temperature controller 18 by means of an adder 25 having the input terminals thereof fed with the power modulation and temperature control signals and having the summing output thereof connected to the control input of power, amplifier 13. The superposed control signal from power modulation generator 24 therefore results in a corresponding power modulation of the average heating power commanded by temperature controller 18.

Figure 2:
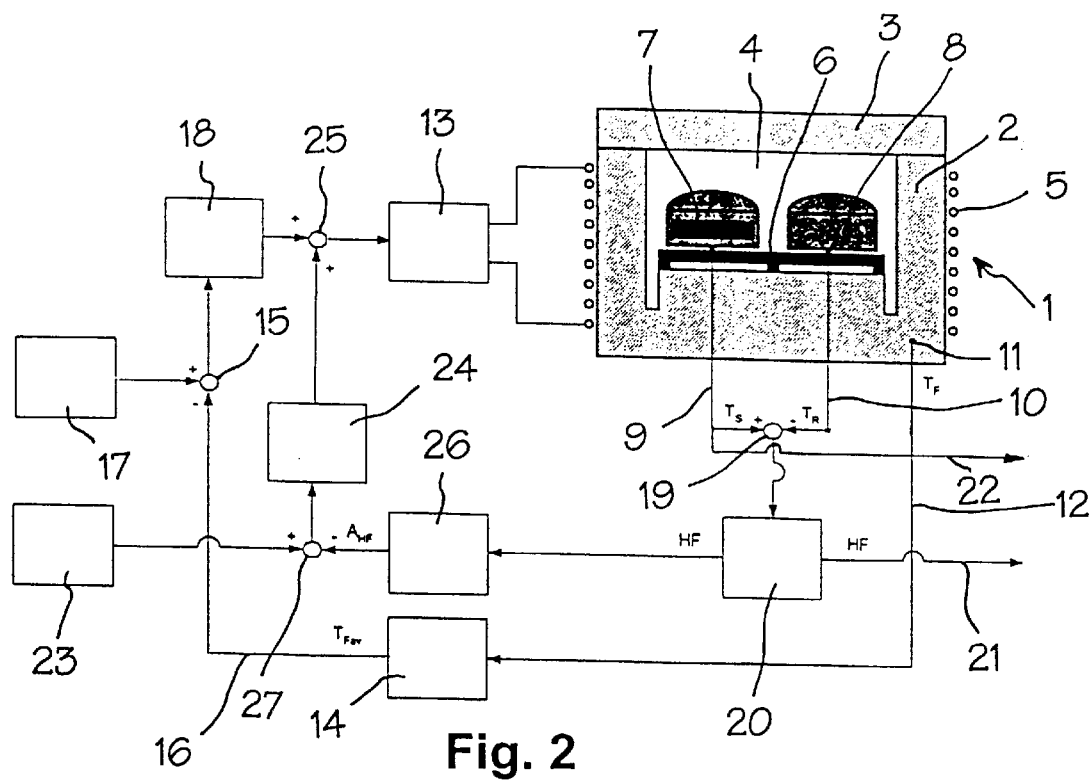
FIG. 2 is a schematic diagram of an embodiment having a different type of controller.

The embodiment schematically illustrated in FIG. 2 is a modification of the embodiment of FIG. 1, and identical reference numerals are used for the same parts of FIGS. 1 and 2. The embodiment of FIG. 2 is different from FIG. 1 by the additional provision of a heat flow demodulator 26 receiving the measured heat flow HF from heat flow calculation unit 20 and outputting a signal which represents a demodulated heat flow amplitude $A_{HF}$ of the measured heat flow HF. The controller further comprises a subtractor 27 having the signal representing the demodulated heat flow amplitude $A_{HF}$ and the second control signal from power modulation programmer 23 applied to the input terminals thereof and delivering a corresponding difference signal to power modulation generator 24. As a result, heat flow calculation unit 20, heat flow demodulator 26, subtractor 27, power modulation generator 24, adder 25 and power amplifier 13 form a second control loop in addition to the first control loop in FIG. 1. This second control loop causes a power modulation of heat source 1 so as to have the amplitude of the measured heat flow HF to assume the amplitude value set by power modulation programmer 23. Otherwise, FIG. 1 is similar to FIG. 2, and reference is in so far made to the above description of FIG. 1.

Figure 3:
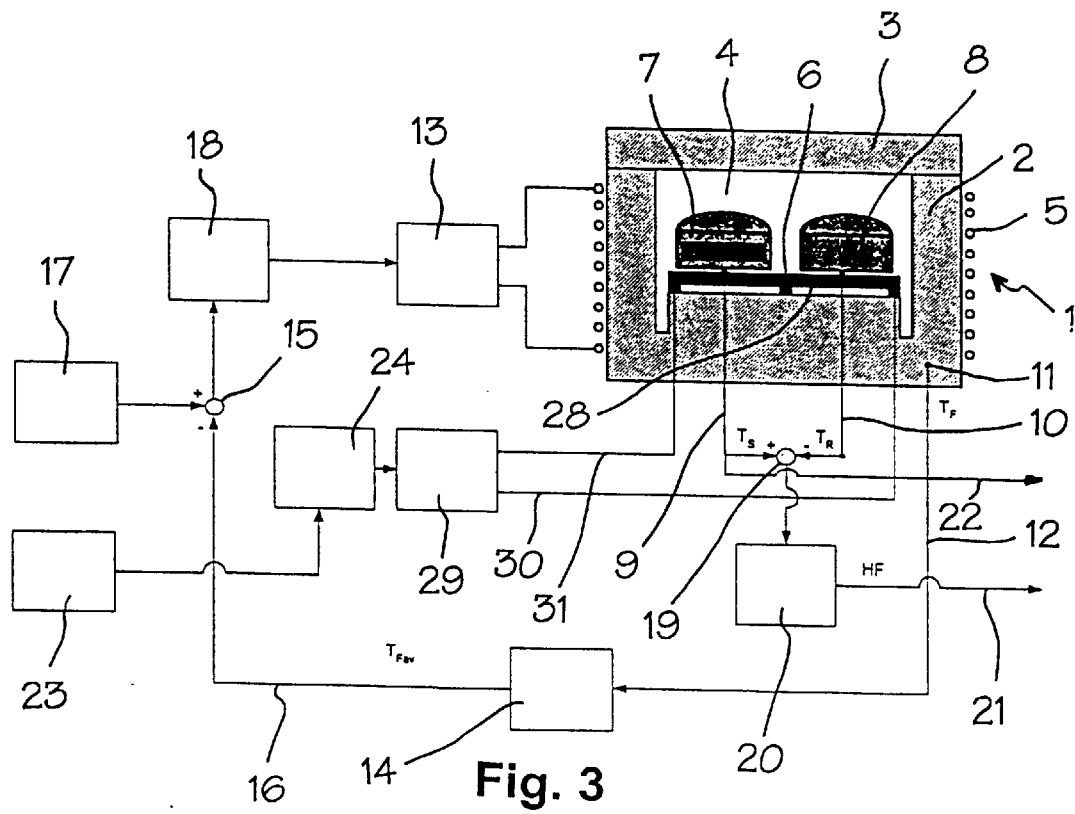
FIG. 3 is an embodiment similar to FIG. 1 but modified by incorporating first and second heaters.

The embodiment schematically illustrated in FIG. 3 is a modification of the embodiment of FIG. 1, and again identical reference numerals are used for the same parts of FIGS. 1 and 3. FIG. 3 is different from FIG. 1 in that a separate heater 28 is formed with substrate 6 to extend over both of the sample and reference pan locations 7, 8. The separate heater 28 is energized by a separate power amplifier 29 via supply lines 30, 31. The separate power amplifier 29 is controlled by the control signal from power modulation generator 24 while the power amplifier 13 energizing heating winding 5 is controlled by the control signal from temperature controller 18. As a consequence, the power modulation is transferred to the sample and reference through the separate heater 28. Otherwise, FIG. 3 is similar to FIG. 1, and reference is in so far made to the above description of FIG. 1.

Figure 4:
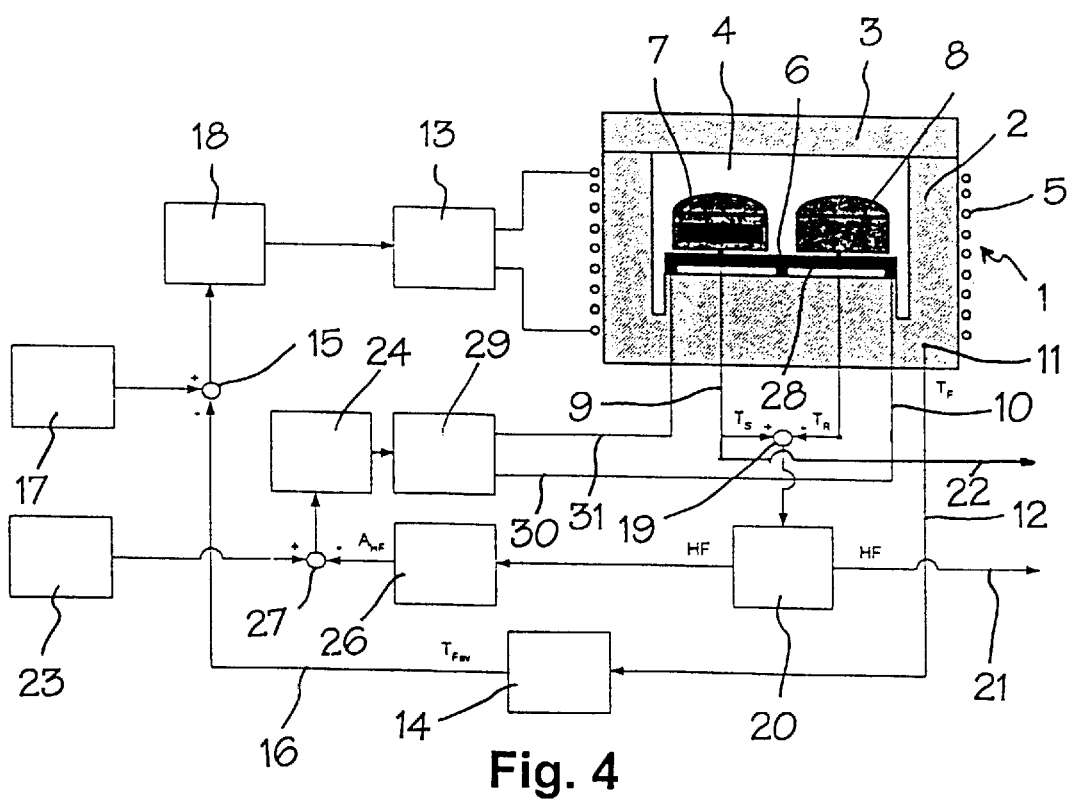
FIG. 4 is an embodiment similar to FIG. 2 but modified by incorporating first and second heaters.

The embodiment schematically illustrated in FIG. 4 is a modification of the embodiment of FIG. 2, and identical reference numerals are used for the same parts of FIGS. 2 and 4. FIG. 4 is different from FIG. 2 in that a separate heater 28 is formed with substrate 6 to extend over both of the sample and reference pan locations 7, 8. The separate heater 28 is energized by a separate power amplifier 29 via supply lines 30, 31. The separate power amplifier 29 is controlled by the control signal from power modulation generator 24 while the power amplifier 13 energizing heating winding 5 is controlled by the control signal from temperature controller 18. As a consequence, the power modulation is transferred to the sample and reference through the separate heater 28. Otherwise, FIG. 4 is similar to FIG. 2, and reference is in so far made to the above description of FIG. 2.

Figure 5:
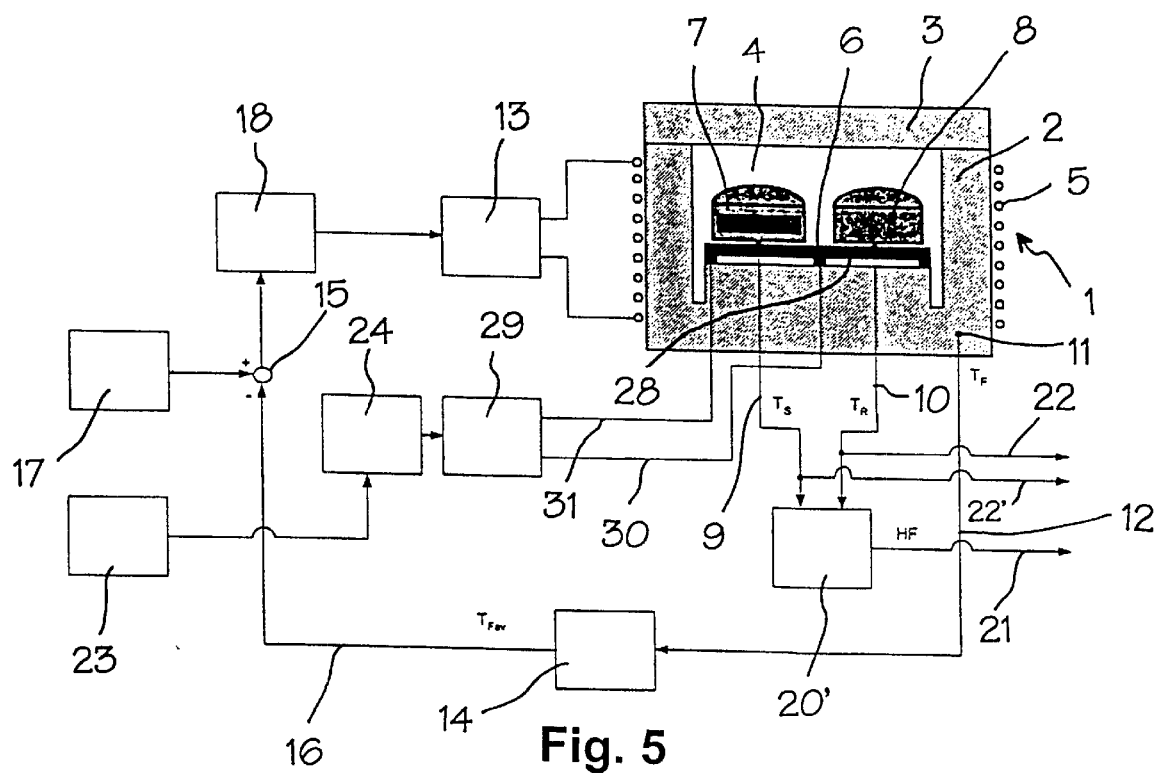
FIG. 5 is an embodiment similar to FIG. 3 but modified in respect of the second heater.
Figure 6:
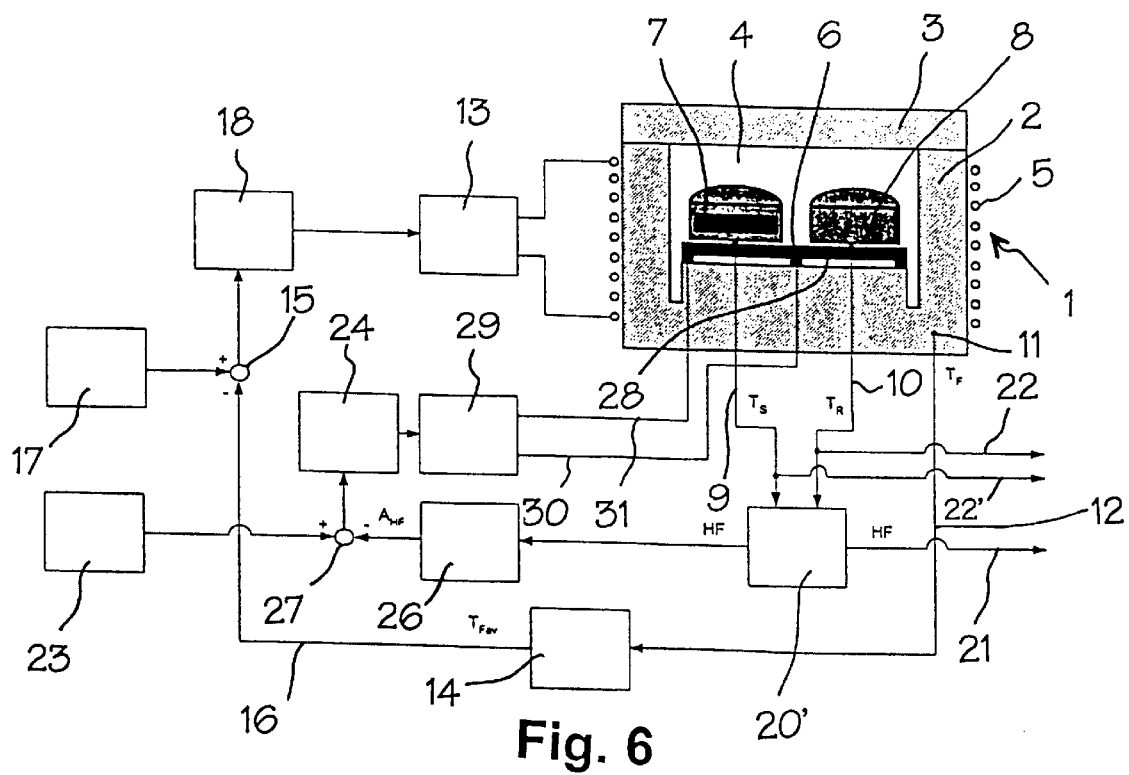
FIG. 6 is an embodiment similar to FIG. 4 but modified in respect of the second heater.

The embodiments schematically illustrated in FIGS. 5 and 6 are modifications of the embodiments of FIGS. 3 and 4, respectively, and identical reference numerals are used for the same parts. The difference in FIGS. 5 and 6 as compared to corresponding FIGS. 3 and 4, respectively, is in the fact that separate heater 28 is only arranged for the sample location 7 and does not extend to the reference location 8 while the signals representing sample temperature $T_S$ and reference temperature $T_R$ on signal lines 9 and 10, respectively, are separately applied to heat flow calculation unit 20' and are separately applied to the evaluation unit (not shown) on signal lines 22, 22'. Otherwise, FIGS. 5 and 6 are similar to FIGS. 3 and 4, respectively, and reference is in so far made to the above description thereof.

The measured heat flow signal HF on signal line 21, the temperature difference signal on signal line 22 and the temperature signals $T_S$ and $T_R$ on signal lines 22 and 22', respectively, each have a dynamical signal component related to the power modulation commanded by the second control signal and an average component related to the temperature-versus-time function commanded by the first control signal. These signals may be evaluated so as to separate between the dynamical and average components to thereby establish separate relations between the dynamical and average components of heat flow HF and at least one of the temperature signal components to thereby collect an optimum amount of information on the physical parameters of the sample.

Figure 7:
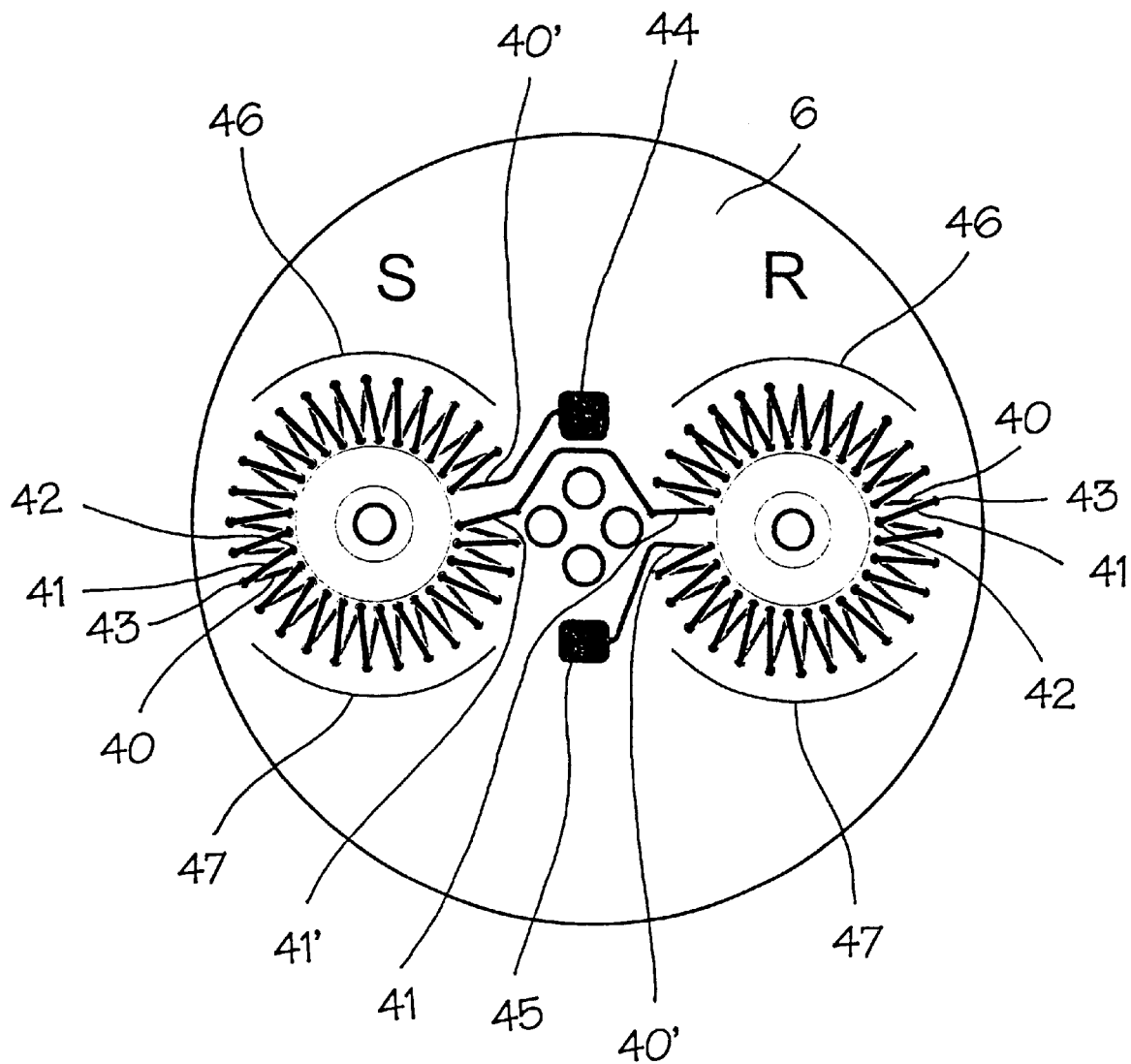
FIG. 7 is an embodiment of a substrate for holding a sample and a reference.

In a particular embodiment illustrated in FIG. 7, the upper side of substrate 6 has two layers of strips 40, 41 of thermocouple ink printed thereon in a pattern so as to form a thermocouple composed of a plurality of series-connected thermosensitive junctions 42, 43 circularly arranged at a sample position S and a reference position R. The thermosensitive junctions 42, 43 are formed between overlapping portions of the lower and upper layers of strips 40, 41 of thermocouple ink. This produces two sets of thermosensitive junctions 42, 43 located on two concentric circles of different radius for each of said sample and reference positions. The thermosensitive junctions 42 and 43 of the two circles are circumferentially spaced under the same angular distance but mutually staggered at half of this angular distance. Each thermosensitive junction 43 on the outer circle is connected with two thermosensitive junctions 42 on the inner circle by a lower layer strip 40 of thermocouple ink and an upper layer strip 41, respectively, the circumferential offset between these connected junctions being one half of the angular distance between the thermosensitive junctions of each circle.

In each of the sample and reference positions S and R. one of the circumferentially adjacent strips 40' and 41' of thermocouple ink of the lower and upper layers, respectively, has a radially outer end thereof connected to each of a connection pad 44, 45, respectively, formed on the upper face of the substrate 6, while the other ones have a radially outer end thereof connected together. Connection pads 44, 45 are located diametrically opposite an imaginary connecting line between the centers of said sample and reference positions S, R.

FIG. 7 further shows for each of said sample and reference positions S, R two diametrically opposite strips 46, 47 in the form of portions of a circle concentrically arranged with the inner and outer circular loci of thermosensitive junctions 42, 43 and radially outside the locus of thermosensitive junctions 43. These two strips 46, 47 act as positional aids to concentrically position a sample pan and reference pan, respectively.

The pattern of strips 40, 41 of thermocouple ink, connection pads 44, 45 including their interconnections and strips 46 and 47 is embedded into a dielectric material providing for electric insulation and is covered by a protective overglaze.

When substrate 6 is used in a heat source 1 as exemplarily illustrated in one of FIGS. 1 to 6, a flow of heat is caused to occur between oven block 2 and a sample of material accommodated in sample pan 7 at sample position S, while the same is the case for reference pan 8 in reference position R. In both cases, the flow path of heat extends across the radial outer circle of thermosensitive junctions 43 and the inner circle of thermosensitive junctions 42. This flow of heat causes a temperature difference to occur between the radially outer and inner thermosensitive junctions 43 and 42, respectively, and the thermocouple formed of the series connection of these thermosensitive junctions 42 and 43 generates an electrical output signal in proportion to said temperature difference. In this signal, a signal portion associated with the heat flow to reference position R is subtracted from the heat flow to sample position S thereby forming a differential heat flow signal.

LIST OF REFERENCE NUMERALS 1 heat source
2 oven block
3 removable lid
4 interior
5 winding of heating wire
6 substrate
7 sample pan
8 reference pan
9 signal line
10 signal line
11 thermometer
12 signal line
13 power amplifier
14 filter
15 subtractor
16 signal line
17 temperature programmer
18 temperature controller
19 subtractor
20, 20' heat flow calculation unit
21 signal line
22, 22' signal line
23 power modulation programmer
24 power modulation generator
25 adder
26 heat flow demodulator
27 subtractor
28 separate heater
29 separate power amplifier
30, 31 supply lines
40, 40', 41, 41' strips of thermocouple ink
42, 43 thermosensitive junctions
44, 45, connection pads
46, 47 strips

What is claimed is:

1. A method for thermally analyzing a material, comprising the steps of:

establishing a heat flow path between a sample of said material and a heat source to thereby cause a flow of heat between said sample and said heat source;

controlling the heating power of said heat source as a function of time;

measuring a signal representative of said heat flow between said sample and said heat source and a signal representative of a temperature associated with said heat flow; and evaluating a functional relation between said measured heat flow and temperature signals;

wherein said step of controlling said heating power is based on a first control input for causing said heat source to assume a predetermined temperature as a function of time and a second control input for modulating the heating power of said heat source caused by said first control input in accordance with a selected periodic power modulation.

2. A method according to claim 1, wherein said second control input is to set a predetermined amplitude of said power modulation.

3. A method according to claim 1, wherein said second control input is to determine said power modulation so as to result in a predetermined amplitude of said measured heat flow.

4. A method according to claim 1, further comprising the steps of measuring a temperature of said heat source;

filtering said measured temperature to thereby derive an average temperature corresponding to the unmodulated heating power of said heat source; and using a signal representative of a difference between said average temperature and said first control input as a heating power control signal for said heat source.

5. A method according to claim 3, further comprising the steps of demodulating said measured heat flow signal to thereby derive an amplitude of said heat flow caused by said power modulation; and using a signal representative of a difference between said demodulated amplitude and said second control input as a heating power control signal for said heat source.

6. A method according to claim 1, further comprising the steps of providing a supplementary heat source in addition to said heat source;

controlling said heat source in accordance with said first control input; and controlling said supplementary heat source in accordance with said second control input.

7. A method according to claim 1, wherein said signal representative of heat flow is a differential signal corresponding to a difference of heat flows between said sample and said heat source and a reference material and said heat source.

8. A method according to claim 6, wherein said supplementary heat source is associated with said sample only.

9. A method according to claim 1, wherein said step of evaluating a functional relation between said measured heat flow and temperature signals comprises the steps of deriving an average component of at least one of said measured heat flow and a heating rate derived from said measured temperature associated with said heat flow over a selected interval of time;

deriving a dynamical component of at least one of said heat flow and heating rate as a difference between said measured heat flow or derived heating rate, respectively, and said respective derived average component;

deriving an average temperature of said measured temperature associated with said heat flow over said selected interval of time; and representing at least one of said dynamical components as a function of said derived average temperature.

10. A method according to claim 1, wherein said step of measuring a signal representative of said heat flow comprises the step of measuring a temperature difference between at least two locations spaced at a distance along said heat flow path.

11. An apparatus for thermally analyzing a material, comprising a heat source (1);

a sample holder (6) having a sample position (7) thermally coupled to said heat source (1, 2) to thereby establish a heat flow path for a flow of heat between said heat source (1) and a sample in said sample position (7);

a controller for controlling the heating power of said heat source (1) as a function of time;

means (9) for measuring a signal representative of said heat flow (HF) between said sample in said sample position and said heat source;

means (11, 12) for measuring a signal representative of a temperature associated with said heat flow (HF);

and means for evaluating a functional relation between said measured heat flow and temperature signals;

wherein said controller comprises means (17) for setting a first control signal representing a selected temperature program of said heat source (1) as a function of time and means (23) for setting a second control signal representing a periodic power modulation of said heating power caused by said first control signal.

12. An apparatus according to claim 11, wherein said controller comprises a filter (14) having a signal representative of a measured temperature ($T_f$) of said heat source (1) applied to an input thereof and producing a signal representative of an average temperature ($T_{Fav}$) of said heat source (1) at an output thereof; and a subtractor (15) having said first control signal applied to one input thereof and having said average temperature signal ($T_{Fav}$) applied to the other input thereof, and producing a temperature control signal for said heat source (1) at an output thereof.

13. An apparatus according to claim 11, wherein said controller comprises a heat flow demodulator (26) for deriving a modulation amplitude ($A_{HF}$) from said measured heat flow (HF); and a subtractor (27) having said second control signal applied to one input thereof and having said derived modulation amplitude ($A_{HF}$) applied to the other input thereof, and producing a power modulation control signal for said heat source (1) at an output thereof.

14. An apparatus according to claim 11, wherein said heat source (1) comprises a first heater (5) controlled in accordance with said first control signal and a second heater (28) controlled in accordance with said second control signal.

15. An apparatus according to claim 11, further comprising a reference holder (6) having a reference position (8) thermally coupled to said heat source (1) to thereby establish a heat flow path for a flow of heat between said heat source (1) and a reference in said reference position (8); and means (19) for measuring a temperature difference between said sample and reference positions (7, 8).

16. An apparatus according to claim 14, wherein said second heat source (28) is associated with said sample position (7) only.

17. An apparatus according to claim 11, wherein said means for measuring a signal representative of said heat flow comprises means for measuring a temperature difference between at least two locations spaced at a distance along said heat flow path.

18. An apparatus according to claim 17, wherein said means for measuring said temperature difference is formed by a thermocouple having at least two thermosensitive junctions (42, 43) positioned along said heat flow path, one of said junctions being closer to said sample position (S) than the other one.

19. An apparatus according to claim 18, wherein said thermocouple comprises two sets of alternatingly series connected thermosensitive junctions (42, 43) arranged on two concentric circles centered around said sample position (S).

20. A calorimeter according to claim 11, wherein said sample position (S) is adapted to receive a sample pan (7) in thermal contact, said sample pan (7) being formed to receive said sample therein.

* * * * *